United States Patent [19]

Nho et al.

[11] Patent Number: 5,234,903
[45] Date of Patent: Aug. 10, 1993

[54] CHEMICALLY MODIFIED HEMOGLOBIN AS AN EFFECTIVE, STABLE NON-IMMUNOGENIC RED BLOOD CELL SUBSTITUTE

[75] Inventors: Kwang Nho, Highland Park; Shmuel Zalipsky, Edison, both of N.J.; Frank Davis, El Cerrito, Calif.

[73] Assignee: Enzon, Inc., South Plainfield, N.J.

[21] Appl. No.: 616,129

[22] Filed: Nov. 20, 1990

Related U.S. Application Data

[63] Continuation-in-part of Ser. No. 440,553, Nov. 22, 1989, abandoned.

[51] Int. Cl.$^5$ .............................................. C07K 15/22
[52] U.S. Cl. ......................................... 514/6; 530/385
[58] Field of Search ............................. 514/6; 530/385

[56] References Cited

U.S. PATENT DOCUMENTS

| | | |
|---|---|---|
| 4,179,337 | 12/1979 | Davis et al. . |
| 4,301,144 | 11/1981 | Iwashita et al. ..................... 530/385 |
| 4,377,512 | 3/1983 | Ajisaka et al. . |
| 4,412,989 | 11/1983 | Iwashita et al. . |
| 4,529,719 | 7/1985 | Tye et al. . |
| 4,584,130 | 4/1986 | Bucci et al. . |
| 4,670,417 | 6/1987 | Iwasaki et al. ..................... 530/385 |
| 4,698,387 | 10/1987 | Schmidt et al. . |
| 4,777,244 | 10/1988 | Bonhard .............................. 530/385 |
| 4,857,636 | 8/1989 | Hsia .................................... 530/385 |
| 4,900,780 | 2/1990 | Cerney . |
| 4,902,502 | 2/1990 | Neteck et al. ......................... 424/83 |
| 5,006,333 | 4/1991 | Saifer et al. ........................... 424/78 |

FOREIGN PATENT DOCUMENTS 2551660  3/1985  France .

OTHER PUBLICATIONS

Isao et al., Chemical Abstract, vol. 75 (No. 15), Abstract No. 947,13h, Oct. 1971.

Taylor et al., Chemical Abstracts, vol. 93 (No. 17), Abstract No. 184604z, Oct. 1980.
Yabuki et al., 1990, Transfusion 30:516–520.
Agishi et al., 1988, Biomat., Art. Cells, Art. Orig. 16:261–270.
Labrude et al., 1988, Int. J. Artif. Organs 11:393–402.
Leonard and Dellacherie, 1988, Makromol. Chem. 189:1809–1817.
Matsushita et al., 1988, Biomat. Art. Cells. Art. Org. 16:247–260.
Nishi et al., 1988, Biomat. Art. Cells, Art. Org. 16:653–655.

(List continued on next page.)

*Primary Examiner*—Lester L. Lee
*Attorney, Agent, or Firm*—Lerner, David, Littenberg, Krumholz & Mentlik

[57] ABSTRACT

The present invention relates to chemically modified hemoglobin produced by a novel and efficient method in which stroma-free hemoglobin is first effectively deoxygenated and reduced and then conjugated with a polyalkylene oxide such as polyethylene glycol (PEG) under conditions which maintain the structural integrity of the heme oxygen binding site. In specific, preferred embodiments of the invention, the deoxygenation and reduction is performed under an inert atmosphere by the amino acid cysteine. In additional specific, preferred embodiments, the structural integrity of the heme oxygen binding site is maintained by a high anionic concentration in the reaction mixture. In further preferred specific embodiments of the invention, the polyalkylene oxide is polyethylene glycol; in still further preferred specific embodiments of the invention, the polyalkylene oxide is linked to hemoglobin via a urethane (carbamate) linkage.

The novel PEG-modified hemoglobin compounds of the invention exhibit superior oxygen transport capabilities, extended half-life, and importantly, low immunogenicity.

8 Claims, No Drawings

OTHER PUBLICATIONS

Iwashita et al., 1988, Biomat., Art. Cells, Art. Org. 16:271–280.
Matsushita et al., 1987, Trans. Am. Soc. Artif. Intern. Organs 33:352–355.
Zygmunt et al., 1987, Int. J. Biol. Macromol. 9:343–345.
Iwasaki et al., 1986a, Artif. Organs 10:470–474.
Iwasaki and Iwashita, 1986b, Artif. Organs 10:411–416.
Matsushita et al., 1986, Trans. Am. Soc. Artif. Intern. Organs 32:490–494.
Leonard and Dellacherie, 1984, Biochem. Biophys. Acta 791:219–225.
Leonard et al., 1984, Tetrahedron 40:1581–1584.
Bunn, *Science*, 172, 1049–50 (1971).
Breepole et al., *Pflugers. Arch.*, 389, 219–20 (1981).
Fronticelli et al., *J. Biol. Chem.*, 259(17), 10841–44 (Sep. 10, 1984).
Bucci et al., *Biomat., Art. Cells, Art. Org.*, 16(1–3), 197–204 (1988).

CHEMICALLY MODIFIED HEMOGLOBIN AS AN EFFECTIVE, STABLE NON-IMMUNOGENIC RED BLOOD CELL SUBSTITUTE

This application is a continuation-in-part of U.S. patent application Ser. No. 07/440,553, filed Nov. 22, 1989 and now abandoned.

TABLE OF CONTENTS

1. Introduction
2. Background Of The Invention
   2.1. Blood Transfusions and Transfusion Reactions
   2.2. Red Blood Cell Substitutes
   2.3. The Chemistry Of Hemoglobin
   2.4. Stroma-Free Hemoglobin
   2.5. Methods For Modifying Hemoglobin For Use As a Red Blood Cell Substitute
   2.6. PEGylation
3. Summary Of The Invention
   3.1. Abbreviations
4. Description Of The Figures
5. Detailed Description Of The Invention
   b 5.1 A Method of Producing Polyalkylene Oxide-Modified Non-Human Hemoglobin
      5.1.1. Reduction Of Hemoglobin
         5.1.1.1. Partial Deoxygenation Of Hemoglobin Prior to Modification
      5.1.2. Conjugation
      5.1.3. Second Reduction
      5.1.4. Sterilization
      5.1.5. Characteristization of Polyalkylene Oxide Modified Hemoglobin
   5.2. Utility Of The Invention
6. Example I: Production Of A Monomeric Bovine Hemoglobin Modified By Monofunctional Poly(ethylene glycol)
   6.1. Materials and Methods
      6.1.1 Bovine Hemoglobin
      6.1.2. Synthesis of Poly(ethylene glycol)-N-succinimdie Carbonate
      6.1.3. Reduction Of Hemoglobin
      6.1.4. Conjugation With Poly(ethylene glycol)-N-succinimide Carbonate
      6.1.5. Second Reduction
   6.2. Results and Discussion
7. Example II: Deoxygenation Of Hemoglobin Using A Gas Permeable Membrane
8. Example III: Conjugation Of Hemoglobin To Monofunctional PEG AT A 30:1 Molar Ratio
9. Example IV: Conjugation Of Hemoglobin To Monofunctional EPG AT A 40:1 Molar Ratio
10. Example V: Production Of Polymerizated Bovine Hemoglobin Modified First By Bifunctional PEG And Then Further Modified By Monofunctional PEG
    10.1. Materails and Methods
       10.1.1. Bovine Hemoglobin
       10.1.2. Synthesis of Poly(ethylene glycol)-Bis-N-Succinimide Carbonate
       10.1.3. Reduction Of Hemoglobin
       10.1.4. Conjugation With BSC-PEG
       10.1.5. Second Reduction
    10.2. Results And Discussion
11. Example VI: in Vivo Studies
12. Example VII: Reducing Agents In Bovine Hemoglobin Solution
    12.1. Materials and Methods
    12.2 Results
13. Example VIII: Partial Deoxygenation Of Hemoglobin By Gas Exchange, And Its Modification Using Monofunctionally Activated Polyethylene Glycol
14. Example IX: Partial Deoxygenation Of Hemoglobin By A chemical Reduction Agent, And Its Modification Using Monofunctionally Activated Polyethylene Glycol
15. Example X: Partial Deoxygenation Of Hemoglobin By Gas Exchange And Its Modification Using Bifunctionally Activated Polyethylene Glycol

1. INTRODUCTION

The present invention relates to chemically modified hemoglobin produced by a novel and efficient method in which stroma-free hemoglobin is first effectively deoxygenated and reduced and then conjugated with a polyalkylene oxide, such as poly(ethylene glycol) (PEG) under conditions which maintain the structural integrity of the heme oxygen binding site. In preferred embodiments of the invention, hemoglobin is only partially deoxygenated prior to chemical modification. The polyalkylene oxide-modified hemoglobin produced according to the methods of the invention has superior oxygen binding properties and can be used as an effective, non-immunogenic and stable red blood cell substitute.

2. BACKGROUND OF THE INVENTION

2.1. Blood Transfusions and Transfusion Reactions

Blood transfusions are used to supplement the hemodynamic system of patients who suffer from a variety of disorders, including diminished blood volume, or hypovolemia (e.g. due to bleeding), a decreased number of blood cells (e.g. due to bone marrow destruction), or impaired or damaged blood cells (e.g. due to hemolytic anemia). Blood transfusions serve not only to increase the intravascular volume, but also to supply red blood cells which carry dissolved oxygen and facilitate oxygen delivery to tissues.

Often, the critical need for a blood transfusion arises acutely. In a previously healthy person, an acute blood loss of as much as 10 percent of the normal blood volume (i.e. about 500 ml) may be compensated for by a constriction of the arteriolar bed and an augmentation in heart rate; however, when blood volume is reduced by 15 to 25 percent (i.e. about 750 to 1250 ml), cardiac output falls markedly. Thereafter, relatively small losses of blood may result in life-threatening reductions of cardiac output, blood pressure, and tissue perfusion. Reduced delivery of oxygen to tissues promotes anaerobic glycolysis, and plasma lactate levels rise (Braunwald and Williams, 1983, in "Harrison's Principles of Internal Medicine", Petersdorf et al., eds. McGraw-Hill Book Company, N.Y., p. 173). It is essential that an adequate blood replacement be immediately available in such situations.

Currently, a number of intravenous fluids are available for the treatment of acute hypovolemia, including crystalloids, such as lactated Ringer's solution or normal saline, and colloidal solutions, such as normal human serum albumin. Crystalloids and colloids temporarily correct the volume deficit, but do not directly supplement oxygen delivery to tissues. Blood transfusion is the preferred mode of treatment; however, there is often a time lag before the blood transfusion may be ordered and administered. Frequently, the patient's exact blood type needs to be determined before donated blood can be ordered. May, in "Emergency Medicine" (1984, John Wiley & Sons, Publ., N.Y., p. 263) comments that, for the critically injured patient, "(t)he type of blood that is given usually depends on the availability in the blood bank at the time." Unfortunately, the amount and variety of blood available for transfusions is inconsistent and unpredictable; for rare blood types, availability is a perpetual problem.

In addition to problems of availability, blood transfusions are associated with a number of clinical complications, which may broadly be classified as immune or non-immune reactions. Among the immunological transfusion reactions is hemolysis (lysis of red blood cells) due to red blood cell alloantibodies, which may occur intravascularly or extravascularly. Extravascular hemolysis is typically associated with antibodies of the Rh system, but several additional antibodies may also be involved (for example, antibodies reactive with antigens of the Kell, Duffy and Kidd systems). Clinical symptoms are generally relatively mild, consisting of malaise and fever. Intravascular hemolysis, however, usually due to incompatibility within the ABO system, is associated with a more severe clinical syndrome, including restlessness, anxiety, flushing, chest or lumbar pain, tachypnea, tachycardia, and nausea, often followed by shock and renal failure (Giblett, in "Harrison's Principles of Internal Medicine," Petersdorf, et al., eds. McGraw-Hill Book Co., N.Y., p. 1915).

Transfusion of non-irradiated blood products has been associated with acute graft versus host disease in immunocompromised patients (von Fliedner et al., 1982, Am. J. Med. 72:951-961; Brubaker, 1986, Hum. Pathol. 17:1085-1088; Kessinger et al., 1987, J. Surg. Oncol. 36:206-209). Recently, however, two cases of fatal transfusion-associated graft versus host disease were reported in immunocompetent patients after cardiac surgery (Thaler et al., 1989, N. Engl J. Med. 321:25-28).

Non-immune transfusion reactions include circulatory overload (especially in patients with renal or cardiac insufficiency), infections, metabolic disturbances, air and fat embolisms, thrombophlebitis, and siderosis. Massive transfusion can result in hyperkalemia, ammonia and citrate toxicity, which may be avoided by using blood stored for no more than a week, and dilutional coagulopathies, which may be obviated by supplementation with platelet concentrates. Siderosis may result from exposure to free iron from hemolyzed blood (Giblett, in "Harrison's Principles of Internal Medicine," Petersdorf et al., eds. McGraw-Hill Book Co., N.Y., p. 1915).

Infections associated with blood transfusions include hepatitis (especially non-A, non-B), cytomegalovirus infection, syphilis, malaria, toxoplasmosis, brucellosis, acquired immune deficiency syndrome (AIDS), and adult T cell leukemia. Beginning in March 1985, voluntary deferral of blood donation by persons at risk for human immunodeficiency virus (HIV) and screening of donated units for HIV-1 antibody have reduced the risk of transfusion-related HIV infection (Ward et al., 1986, JAMA 256:357-361; Ward et al., 1988, N. Engl. J. Med. 318:473-478). However, rare cases of HIV transmission by pre-screened blood components has been reported (MMWR, 1986, 35:389-391). Imagawa et al. (1989, N. Engl. J. Med. 320:1458-1462) reported the isolation of infectious HIV-1 virus from 31 of 133 high-risk individuals who tested negative for antibodies on conventional ELISA and Western blot assay. Further, the screening of donated blood units for antibodies to HTLV-I (the causative agent of a form of human T cell leukemia) has recently been recommended by the FDA (MMWR, 1988, 37:736-747). Cohen et al. (1989, N. Engl. J. Med. 320:1172-1176) reported that the observed risk of HIV-1 transmission was 0.003 percent per unit of blood; the risk of HTLV-I infection was found to be 0.024 percent per unit of blood transfused.

2.2. Red Blood Cell Substitutes

In addition to crystalloid and colloidal intravenous volume expanders, several red blood cell substitutes have been developed within the past 15-20 years which have oxygen-transporting capability. For example, perfluoro compounds (e.g. Fluosal-DA and Oxypherol) have been experimentally used as blood substitutes in humans (Gould et al., 1986, N. Engl. J. Med. 314:1653-1656); for review of perfluoro compounds as blood substitutes, see also Riess et al. (1978, Angew Chem. Int. Ed. Engl. 17:621-634). Additionally, acellular hemoglobin preparations have been developed as alternative red blood cell substitutes.

2.3. The Chemistry of Hemoglobin

Native hemoglobin exists as a tetramer consisting two $\alpha$ chains and two $\beta$ chains. Each $\alpha$ and $\beta$ chain binds a heme residue in a noncovalent linkage. The $\alpha$ and $\beta$ chains are also held together by noncovalent bonds resulting from hydrogen bonding and van der Waals forces. The four heme groups, one in each subunit, are capable of binding four molecules of oxygen. These heme groups, flat molecules in which the iron atoms form square-planar coordination complexes, are situated relatively far apart from one another in the intact molecule (Lehninger, 1975, in "Biochemistry," Worth Publishers, Inc., N.Y. pp. 145-149).

Hemoglobin constitutes about 90% of the total protein in red blood cells. 100 ml of whole blood is capable of absorbing approximately 21 ml of gaseous oxygen due to the binding ability of hemoglobin. Equally important to the binding of oxygen, hemoglobin is also efficient in releasing the bound oxygen to tissues. The ability of hemoglobin to bind and release oxygen is often quantitatively expressed as the $P_{50}$, the partial pressure of oxygen which results in fifty percent saturation of hemoglobin.

The relationship between partial pressure of oxygen and percent saturation of hemoglobin may be represented as a sigmoidal curve, the position of which is affected by pH (the Bohr effect). The higher the pH of the hemoglobin solution at a given partial pressure of oxygen, the greater the percent saturation with oxygen, and the lower the $P_{50}$; the oxygen saturation curve is shifted to the left on the abscissa. Conversely, the lower the pH of the hemoglobin solution, the lower the percent saturation with oxygen, and the higher the $P_{50}$; the oxygen saturation curve is shifted to the right on the abscissa. Thus, as hemoglobin moves from the relatively alkaline pH of the lungs to the relatively acidic pH of oxygen-poor tissues (producing lactic acid by anaerobic respiration), the hemoglobin molecule will have a tendency to release its load of oxygen.

Modifications of the hemoglobin molecule or its conformation may be associated with changes in oxygen binding affinity. For example, association with 2,3 diphosphoglycerate (2,3 DPG) loosens the association between oxygen and hemoglobin, facilitating release of oxygen to tissues; serum levels of 2,3 DPG rise under physiologic conditions in which an increased delivery of oxygen is desirable, for example, at high altitudes and during pregnancy. Conversely, if the iron ion in the heme prosthetic group is oxidized from Fe(II) to Fe(III), the molecule, having become methemoglobin, binds oxygen so tightly as to preclude oxygen transfer.

2.4. Stroma-Free Hemoglobin

In attempts to utilize free hemoglobin as a red blood cell substitute, erythrocyte hemolyzates have been administered by infusion. However, the stromal components were found to be extremely toxic, resulting in coagulopathy and associated renal failure. In 1967, Rabiner used centrifugation and ultrafiltration procedures to prepare a stroma-free hemoglobin solution (Rabiner et al., 1967, J. Exp. Med. 126:1127); by 1977, a crystalline form of stromafree hemoglobin had been prepared (De Venuto et al., 1977, J. Lab. Clin. Med. 89:509).

Stroma-free hemoglobin, taken out of the red blood cell microenvironment, was found to exhibit a propensity to bind oxygen too tightly (a low $P_{50}$) and also to have a short circulating half-life following transfusion. The low $P_{50}$, reflective of a leftward shift in the hemoglobin oxygen binding curve, was, in part, consequent to exposure of stroma-free hemoglobin to a higher pH in plasma (7.4) than that experienced within the erythrocyte (7.2); furthermore, the natural association between hemoglobin and 2,3-diphosphoglycerate was destroyed when hemoglobin was removed from the red cell. In terms of clearance, the stroma-free hemoglobin was observed to be rapidly eliminated by the kidneys, with a transfusion half-life of only about 100 minutes.

A number of chemical modifications have been introduced into stroma-free hemoglobin in attempts to increase the $P_{50}$ and to render the hemoglobin more stable. Perhaps the most widely used chemical modification of stroma-free hemoglobin utilizes pyridoxal 5'-phosphate and sodium or potassium borohydride to increase the $P_{50}$ (Benesch et al., 1972, Biochem. 11:3576).

To extend the half-life of stroma-free hemoglobin, the hemoglobin has been linked to other macromolecules, such as dextran (Chang, J. E. et al., 1977, Can. J. Biochem. 55:398), hydroxyethyl starch (DE OS No. 2,616,086), gelatin (DE AS 2,449,885), albumin (DE AS 2,449,885), and polyethyleneglycol (PEG) (DE 3026398; U.S. Pat. No. 4,670,417; U.S. Pat. No. 4,412,989; U.S. Pat. No. 4,301,144). Technologies were also developed to cross-link stroma-free hemoglobin to form polyhemoglobin (U.S. Pat. No. 4,001,200 and 4,001,401) or to internally cross-link hemoglobin molecules, for example, using 2-N-2-formyl-pyridoxal-5'-phosphate and borohydride (Benesch et al., 1975, Biochem. Biophys. Res. Commun. 62:1123) or diaspirins (diesters of bis 3,5-dibromosalicylate; see U. S. Pat. No. 4,529,719).

Additional modifications of stroma-free hemoglobin included a method for decreasing the rate of methemoglobin formation using NADH and NADPH (Sehgal et al., 1981, J. Surg Res. 31:13–17). Keipert and Chang (1985, Biomater. Med. Devices Artif. Organs 13:156) tested the efficacy of pyridoxal phosphate treated polyhemoglobin in resuscitating rats acutely bled to 67 percent of total blood volume, and found it comparable to whole blood in providing for long-term survival.

The use of stroma-free hemoglobin from different species as a human red blood cell substitute has been suggested (e.g., in U.S. Pat. No. 4,670,417; U.S. Pat. No. 4,584,130; U.S. Pat. No. 4,529,719; U.S. Pat. No. 4,412,989; U.S. Pat. No. 4,377,512; U.S. Pat. No. 4,301,144; U.S. Pat. No. 4,061,736). However, Chang et al. (1987, Biomater. Artif. Cells Artif. Organs 15:443–452) performed immunologic studies which revealed that immunizing doses of heterologous (i.e. cross-species) hemoglobin was associated with antibody production by the recipient animal; furthermore, cross-linking the heterologous hemoglobin increased the immune response, thereby teaching against the use of cross-species hemoglobins as human red blood cell substitutes.

2.5. Methods for modifying Hemoglobin for Use as a Red Cell Substitute

The following is a review of a number of methods used to modify hemoglobin for use as a red cell substitute.

U.S. Pat. No. 4,777,244 by Bonhard et al., filed May 8, 1987, issued Oct. 11, 1988 relates to the use of an oxygen-consuming reducing agent such as ascorbic acid, reduced glutathione, or reduced methylene blue to increase the proportion of deoxyhemoglobin in stroma-free hemoglobin. The hemoglobin was further modified by an effector substance, such as pyridoxal phosphate or inositol hexaphosphate. A dialdehyde was then used to cross-link the modified hemoglobin, which, subsequently, was reacted with a carbonyl-group specific reducing agent. The product was reported to have a $P_{50}$ of approximately 36 mbar. Experimental data indicates a product methemoglobin content of 5.1%, a $P_{50}$ of 38.6, and a colloid osmotic pressure of 36.8 mbar.

U.S. Pat. No. 4,670,417 by Iwasaki et al., filed Feb. 21, 1986, issued Jun. 2, 1987, relates to a hemoglobin combined with a polyalkylene oxide wherein an amino group of the hemoglobin was bonded to a carboxyl group of an ether-containing polyalkylene oxide via an amide linkage. The reaction system was purged of oxygen, which was replaced by an inert gas. A stabilizing agent (e.g. sodium sulfite, sodium bisulfite, Fe(II) sulfate, EDTA, etc.) was added to the final product, to which glucose and/or mannitol was also added to decrease methemoglobin formation. Experimental data indicated that the $P_{50}$ values of various products were 13.7, 6.1, and 12 mm Hg. 2.92% methemoglobin was reported.

U.S. Pat. No. 4,584,130 by Bucci et al., filed Mar. 29, 1985, issued Apr. 22, 1986, relates to stroma-free hemoglobin cross-linked by reagents that mimic 2,3-diphosphoglycerate. Experimental data indicated that modified human hemoglobin with a $P_{50}$ of 26.95 could be produced and that mddified bovine hemoglobin exhibited a $P_{50}$ of 40.17 mm Hg.

U.S. Pat. No. 4,529,719 by Tye et al., filed May 4, 1983, issued Jul. 16, 1985, relates to stroma-free hemoglobin deoxygenated using a vacuum and then cross-linked, in an inert atmosphere, with a bis-diaspirin ester, and subsequently reacted with pyridoxal phosphate. Experimental data indicated that modified hemoglobin product was associated with a $P_{50}$ of 32 mm Hg and a half-life of approximately 20 hours.

U.S. Pat. No. 4,412,989, by Iwashita et al., filed Jun. 3, 1982, issued Nov. 1, 1983 relates to hemoglobin or a hemoglobin derivative covalently coupled through an amide bond to a polycarboxylic acid which was in turn linked to a polymer selected from the group consisting of PEG, polypropylene glycol, and copolymers of ethylene oxide and propylene oxide. The reaction system was not deoxygenated, effector molecules, including pyridoxal phosphate, carbonyl hemoglobin, and glucose 6-phosphate derivatives were used in the examples, and PEG was reacted with hemoglobin in the presence of a condensing agent such as carbodiimide and dimethylformamide. Experimental data indicated that the modified hemoglobin product of example sections had a $P_{50}$ ranging from 3.1 to 13.5 and a maximal half-life of 250 min.

U.S. Pat. No. 4,377,512, by Ajisaka and Iwashita, filed Jun. 26, 1981, issued Mar. 22, 1983, relates to hemoglobin modified by linkage to insulin; a maximal half-life of 120 minutes was reported.

U.S. Pat. No. 4,301,144 by Iwashita and Ajisaka, filed Jul. 10, 1980, issued Nov. 17, 1981, relates to modified hemoglobin produced by reacting a polyalkylene glycol with hemoglobin in the presence of a condensing agent, such as cyanogen bromide, or a cross-linking reagent, such as cyanuric chloride. In experimental examples, a maximum $P_{50}$ of 19.5 mm Hg and a maximal half-life of 150 minutes were reported.

2.6. Pegylation

PEGylation is a process in which polypeptides, such as enzymes and hormones, are coupled to polyethylene glycol so as to produce a physiologically active non-immunogenic water soluble polypeptide composition. The polyethylene glycol protects the polypeptide from loss of activity and the composition can be injected into the mammalian circulatory system with substantially no immunogenic response. The process of PEGylation is described in detail in U.S. Pat. No. 4,179,337, entitled "Non-Immunogenic Polypeptides" by Davis et al., filed Jul. 28, 1977, issued Dec. 18, 1979, which is incorporated by reference in its entirety herein.

3. SUMMARY OF THE INVENTION

The present invention relates to chemically modified hemoglobin produced by a novel and efficient method in which stroma-free hemoglobin is first effectively deoxygenated and reduced and then conjugated with a polyalkylene oxide such as polyethylene glycol (PEG) under conditions which maintain the structural integrity of the heme oxygen binding site. In specific, preferred embodiments of the invention, the deoxygenation and reduction is performed under an inert atmosphere by the amino acid cysteine. In additional preferred embodiments, the structural integrity of the heme oxygen binding site is maintained by a high anionic concentration in the reaction mixture. In further preferred specific embodiments of the invention, the polyalkylene oxide is polyethylene glycol; in still further preferred specific embodiments of the invention, the polyalkylene oxide is linked to hemoglobin via a urethane (carbamate) linkage.

The novel PEG-modified hemoglobin compounds of the invention exhibit superior oxygen transport capabilities, extended half-life, and importantly, low immunogenicity. In a specific embodiment of the invention, PEG-modified bovine hemoglobin offers the following advantages:

(i) derivation of hemoglobin from a bovine source effectively precludes the risk of hepatitis, HIV, or HTLV transmission by PEG-bHb products;
(ii) the oxygen binding properties of the PEG-bHb of the invention renders these compounds effective vehicles for oxygen transport;
(iii) the PEG-bHb of the invention is stable, thereby permitting its clinical use as a blood cell substitute and volume expander;
(iv) PEG-bHb has a physiologically advantageous oncotic pressure which deters "third-space" dissemination of fluid as well as diuresis;
(v) PEG-bHb is available in quantity at relatively low prices, and is stable either dried or in solution;
(vi) the low immunogenicity of PEG-bHb diminishes the risk of an allergic transfusion reaction;
(vii) PEG-bHb used as a red blood cell substitute precludes the development of graft versus host disease;
(viii) PEG-bHb is associated with an unexpectedly low free iron concentration, thereby diminishing the potential for iron toxicity and accumulation; and
(ix) PEG bHb exhibits decreased Hb dimer formation.

Of note, polyalkylene oxide-hemoglobin conjugates known in the art, such as those described in U.S. Pat. No. 4,670,471 by Iwasaki et al. (filed Feb. 21, 1986, issued Jun. 2, 1987), U.S. Pat. No. 4,412,989 by Iwashita et al. (filed Jun. 3, 1982, issued Nov. 1, 1983), and U.S. Pat. No. 4,301,144 by Iwashita and Ajisaka (filed Jul. 10, 1980, issued Nov. 17, 1981) were reported to have $P_{50}$ values significantly lower, and degradation rates markedly higher than those of the modified hemoglobin compounds of the present invention. The present invention provides for chemically modified hemoglobin conjugated to polyalkylene oxide and having a $P_{50}$ of at least about 20 mmHg.

In various embodiments, the method of the invention produces a monomeric hemoglobin (modified by monofunctional polyalkylene oxide). Alternatively, the method of the invention may produce a polymeric hemoglobin, modified first by a bifunctional polyalkylene oxide and then further modified by a monofunctional polyalkylene oxide.

The present invention also relates to methods for preparing hemoglobin for subsequent chemical modification comprising partially deoxygenating the hemoglobin prior to chemical treatment. It is based, in part, on the observation that when partially deoxygenated hemoglobin was chemically modified, the resulting hemoglobin product had a higher $P_{50}$ value (indicating superior oxygen delivery capability) compared to chemically modified fully deoxygenated hemoglobin. By producing hemoglobin capable of superior oxygen delivery, the present invention provides for pharmaceutical compositions comprising hemoglobin which are effective volume expanders and efficient vehicles for oxygen transfer in patients in need of such treatment.

| 3.1. ABBREVIATIONS | |
|---|---|
| bHb | bovine hemoglobin |
| BSC-PEG | poly(ethylene glycol)-bis-N-succinimide carbonate |
| deoxy Hb | deoxyhemoglobin |
| 2,3 DPG | 2,3 diphosphoglycerate |
| Hb | hemoglobin |
| GSH | reduced glutathione |
| Met-Hb | methemoglobin |
| oxy-Hb | oxygenated hemoglobin |
| PEG | polyethylene glycol |
| SC-PEG | poly(ethylene glycol)-N-succinimide carbonate |

4. DESCRIPTION OF THE FIGURES

No Figures are being relied upon.

5. DETAILED DESCRIPTION OF THE INVENTION

The present invention relates to novel polyalkylene oxide-modified hemoglobin compounds with superior oxygen transport capabilities, extended half-life, and low immunogenicity. The invention also relates to a novel method for the production of polyalkylene oxide-modified hemoglobin. The polyalkylene oxide-modified hemoglobin compounds of the invention can be used as effective red blood cell substitutes in humans or animals in need of such treatment.

For clarity of disclosure and not by way of limitation, the present invention will be described in the following subsections:
(a) A method of producing polyalkylene oxide-modified hemoglobin;
  (i) Reduction of Hemoglobin
  (ii) Partial Deoxygenation of Hemoglobin Prior to Modification
  (iii) Conjugation
  (iv) Second Reduction
  (v) Sterilization
  (vi) Characterization of Polyalkylene Oxide-Modified Hemoglobin
(b) Utility of the invention.

5.1. A Method of Producing Polyalkylene Oxide-Modified Non-Human Hemoglobin

Huamn or non-human hemoglobin may be used according to the invention. In preferred embodiments, non-human hemoglobin from any appropriate animal source, including, but not limited to, bovine, ovine, equine and porcine hemoglobin, may be used according to the invention. In preferred embodiments of the invention, bovine hemoglobin (bHb) may be used; bovine hemoglobin is readily available in large quantities and exhibits advantageous oxygen-binding characteristics; unlike human hemoglobin, bovine hemoglobin does not require modification by an effector agent such as pyridoxal phosphate in order to achieve physiologically useful oxygen affinity.

5.1.1. Reduction of Hemoglobin

In order to optimize oxygen carrying capacity, the hemoglobin of the invention is initially treated with an agent or agents which (i) deoxygenate hemoglobin to produce deoxyhemoglobin (deoxy Hb) and (ii) reduce the hemoglobin to decrease the methemoglobin (hemoglobin carrying Fe(III) ion) content. In preferred specific embodiments of the invention, the hemoglobin is only partially deoxygenated prior to modification in order to increase the $P_{50}$ of the modified product (see Section 5 1.1.1., infra). Preferably, reduction is carried out in an oxygen free, inert atmosphere. The reduction can be accomplished by using either chemical reducing agents or a gas exchange method. Gas exchange can be successfully achieved by recirculating the Hb solution through gas-permeable hollow fiber membranes against pressurized inert gases such as nitrogen, helium or argon. The commercially available gas-permeable membranes (so called oxygenators) are made of polypropylene or cellulose acetate). A variety of chemical reducing agents may also be used in conjunction with known oxygen scavengers; such reducing agents, include, but are not limited to, sodium ascorbate, glutathione, N-acetyl cysteine, and N-acetyl methionine; however, in preferred embodiments of the invention, cysteine is used to both deoxygenate and reduce the hemoglobin. As shown in Example Section 12, infra, cysteine has been found to be superior to other agents in optimizing the percentage of deoxyhemoglobin while minimizing the amounts of methemoglobin and free iron.

In a preferred, specific embodiment of the invention, bovine hemoglobin may be reduced using cysteine according to the following method:

Bovine hemoglobin, (bHb) which may be obtained from a commercial source (such as Biopure, MA) may be prepared as follows. A solution of about five to eight percent bHb in 0.1 M Na-phosphate, 0.1 M NaCl buffer may be prepared, to which is added cysteine, to a final concentration of between 1 and 100 millimolar, and preferably between 1 and 30 mM. Reaction is then carried out at a temperature of about 4° C. under an inert atmosphere (e.g. a nitrogen atmosphere) and at a pH of 7.5-8.5, in the presence of about 0.01-0.5 M NaCl and about 0.01-0.1 M $NaHCO_3$. Reaction is allowed to proceed for between 1-6 hours, and preferably for between 1 and 2 hours, in order to deoxygenate oxy-bHb and to reduce Met-bHb. After about 6 hours the amount of oxy-bHb should be less than approximately 1 percent and the amount of Met-Hb should be less than about 0.5 percent.

Following completion of the reaction, reduced hemoglobin may be separated from cysteine by any method known in the art. In a preferred embodiment of the invention, ultrafiltration, using an ultrafiltration membrane with a molecular weight limit of 30k-50k, may be used to remove cysteine as well as any dimerized bHb subunits

5.1.1.1. Partial Deoxygenation of Hemoglobin Prior To Modification

The present invention also relates to a method for preconditioning hemoglobin prior to chemical modification comprising partially but not completely deoxygenating the hemoglobin. It is known in the art that some degree of deoxygenation is necessary prior to chemical modification in order to provide a modified hemoglobin with the structural stability of deoxyhemoglobin so that the modified hemoglobin can withstand the physical stresses of chemical modification, diafiltration and/or sterile filtration and sterilization. Furthermore, if hemoglobin subunits are to be crosslinked deoxygenation of the hemoglobin may be required in order to render the reactive site at Lys 99 of the alpha chain accessible to cross-linking agent.

The present invention is based, in part, on the results of experiments exemplified in Sections 13 through 15, infra, in which it was observed that partial but not complete deoxygenation was associated with optimal $P_{50}$ values. Hemoglobin which may be preconditioned according to the invention includes stroma-free hemoglobin derived from human or non-human sources, for example, porcine, bovine, ovine, or equine sources. For purposes of deoxygenation, the hemoglobin may preferably be in aqueous solution, and may preferably be in a concentration of about 1 to 10 percent (w/v). In preferred specific embodiments, the hemoglobin solution may comprise an electrolyte composition of about 0.05-1.0 M NaCl, 0.05-0.5 M Na-phosphate, and 0.01-0.1 M $NaHCO_3$, and a pH between about 7.4 and 8.8. Hemoglobin may, in particular embodiments of the invention, be largely oxygenated prior to preconditioning, such that the process of preconditioning comprises deoxygenating the hemoglobin. Alternatively, in certain embodiments of the invention, the hemoglobin may be substantially deoxygenated such that the process of preconditioning comprises reintroducing a limited amount of oxygen into the hemoglobin. The final percentage of deoxygenated hemoglobin is preferably between about 50 and 80 percent according to the invention.

Therefore, in particular embodiments, the invention provides for methods comprising exposing oxygenated hemoglobin to an inert gas such that (i) oxygen is removed from the hemoglobin and (ii) the final percentage of deoxyhemoglobin is between about 50 and 80 percent. In alternative embodiments, the invention provides for methods comprising exposing deoxygenated hemoglobin to oxygen such that the final percentage of deoxyhemoglobin is between about 50 and 80 percent. Because deoxygenation may be easier to control, the former process may be preferable to the latter process.

Gas exchange may be effected by any method known in the art. For example, and not by way of limitation, deoxygenation of hemoglobin may be performed by exposing a hemoglobin solution to an inert gas, such as (but not limited to) nitrogen, argon or helium. Alternatively, completely deoxygenated hemoglobin may be partially reoxygenated by exposing a deoxygenated hemoglobin solution to oxygen, or to a gas comprising a proportion of oxygen. It may be desirable to optimize the surface area of hemoglobin exposed to the gas, and/or to circulate the hemoglobin such that levels of deoxygenation are relatively homogeneous throughout the solution. According to the present invention, it is important to be able to monitor the level of deoxygenation of hemoglobin in solution. Such monitoring may preferably be continuous so as to permit the termination of the gas-exchange process when desirable levels of deoxyhemoglobin have been attained. For example, and not by way of limitation, such monitoring may be carried out by an OSM3 Hemoximeter (Radiometer, Copenhagen).

In preferred embodiments of the invention, gas exchange may be accomplished through a gas-permeable membrane, including but not limited to a polypropylene or cellulose acetate membrane. For example, gas-exchange devices which are commercially available may be used, including the Celgard ™ polypropylene microporous hollow fiber device from Hoechst-Celanese, or the Cell-Pharm ™ hollow fiber oxygenator from American Fluid, or any other commercially available or non-commercially available device in which gas and hemoglobin are circulated through separate compartments. In a preferred, specific embodiment of the invention, hemoglobin which consists substantially of oxyhemoglobin may be deoxygenated by circulating the hemoglobin in aqueous solution of about 6% Hb (g/dl), 0.5 M NaCl, 0.1 M $Na_2HPO_4$, and 0.05 M $NaHCO_3$, at a pH of about 7.8 and at a temperature of about 4°-6° C., throuqh a Hoechst-Celanese Celgard ™ polypropylene microporous hollow fiber gas exchange device, having thin hollow fiber membranes with inside diameter of about 200 micron to minimize foam formation at a flow rate of about 10-100 ml/min/ft² surface area while supplying said device with nitrogen at a pressure of about 5-20 p.s.i. Hemoglobin may preferably be circulated for about 5 to 30 minutes to result in a final percentage of deoxyhemoglobin of between about 50 and 80 percent. Another method for producing deoxygenated hemoglobin comprises exposing a hemoglobin solution to a chemical reducing agent, including, but not limited to, sodium ascorbate, sodium dithionate and sodium bisulfite. Concentration of the chemical reducing agent, and/or reaction time or temperature, may be adjusted so as to produce a partially deoxygenated hemoglobin product. Alternatively, a reducing agent may be used to substantially deoxygenate hemoglobin, and then oxygen may be reintroduced to form a partially deoxygenated product. In a preferred specific embodiment of the invention, a hemoglobin solution may be exposed to about a 100 mM concentration of sodium bisulfite for about one hour prior to chemical modification.

Preconditioned, partially deoxygenated hemoglobin may then be chemically modified using any method known in the art. In preferred embodiments of the invention, the preconditioned hemoglobin may be modified by conjugation to an activated polyalklyene oxide as described infra. Other methods of chemical modification include but are not limited to alternative methods for conjugation to polyalkylene oxide, reaction with pyridoxal phosphate, reaction with a dialdehyde, reaction with reagents such as 2, 3 diphosphoglycerate (2,3-DPG) or chemically similar compounds, or reaction with bis-diaspirin ester. Hemoglobin may also be uncrosslinked, intramolecularly crosslinked, or intermolecularly crosslinked according to the invention.

The resulting modified hemoglobin may then be tested to determine its $P_{50}$ value so as to confirm that a clinically useful $P_{50}$ has been achieved. Methods of $P_{50}$ measurement include standard methods of analysis, such as, for example, methods utilizing the Hemox-Analyzer (TCS Medical Products Co., Huntingdon Valley, Pa.).

5.1.2. Conjugation

Following reduction, the hemoglobin may be reacted with an activated polyalkylene oxide under conditions which maintain the structural integrity of the oxygen binding site. In preferred embodiments of the invention, such conditions consist of a high anion concentration; in a specific embodiment this anion is chloride ion. In preferred embodiments, the chloride ion concentration is at least about 1.0M. As shown in Table I, the $P_{50}$ of modified hemoglobin has been observed to rise in conjunction with increased chloride ion concentration. According to the invention, the activated polyalkylene oxide may have one or more than one functional groups. The degree of modification for each preparation referred to in Table I is approximately 20 percent. This percent modification corresponds to about 9.2 PEG molecules per each molecule of hemoglobin. The percent modification may be calculated according to the number of lysines modified by PEG and is based on a total of 48 surface lysines in bovine hemoglobin. The number may be determined by trinitrobenzene sulfonic acid (TNBS) assay (Habeef et al., 1966, Analyt. Biochem. 14:328-336).

TABLE I

| $[Cl^-]$, of Reaction Solution, [M] | $P_{50}$(mm Hg) of SC-PEG(2000)-bHb | $P_{50}$ of SC-PEG(4000)-bHb | $P_{50}$ of SC-PEG(5000)-bHb |
|---|---|---|---|
| 0.1 | 24 | 24 | 22 |
| 0.5 | 30 | 28 | 24 |

TABLE I-continued

| [Cl⁻], of Reaction Solution, [M] | $P_{50}$(mm Hg) of SC-PEG(2000)-bHb | $P_{50}$ of SC-PEG(4000)-bHb | $P_{50}$ of SC-PEG(5000)-bHb |
|---|---|---|---|
| 1.0 | 32 | 30 | 29 |
| 1.5 | 31 | 30 | 30 |
| 2.0 | 32 | 30 | 30 |

Polyalkylene oxides which may be used according to the invention for conjugation to hemoglobin include but are not limited to polyethylene oxide, polypropylene oxide, or copolymers of ethylene oxide and propylene oxide; the polyalkylene oxides of the invention may advantageously be water soluble. In a preferred embodiment of the invention, polyethylene glycol may be conjugated to hemoglobin. Preferred molecular weights for polymer may be between 500 and 40,000 Da, and, more preferably, between 1900 and 20,000 Da.

Any method known in the art may be used to activate the polyalkylene oxide for subsequent conjugation to hemoglobin. For example, hydroxyl groups of polyethylene glycol (PEG) may be activated using cyanuric chloride (Abuchowski and Davis, 1981, in "Enzymes as Drugs, Holsenberg and Roberts, eds., John Wiley and Sons, N.Y. pp. 367-383); however, the toxicity of cyanuric chloride requires careful attention to its removal following reaction. Alternatively, polyalkylene oxides may be activated by derivatization to form the corresponding succinoyl-N-hydroxy succinimide ester (Abuchowski et al., 1984, Cancer Biochem. Biophys. 7:175-186), although the ester linkage between the polymer and the succinic acid residue has been associated with limited stability in aqueous media (Iwasaki et al., 1987, U.S. Pat. No. 4,179,337).

In a preferred embodiment of the invention, the polyalkylene oxides may be activated so as to produce urethane linkages with the ε-amino groups of hemoglobin, the urethane linkage being less susceptible to hydrolytic degradation (Larwood and Szoka, 1984, J. Labelled Compounds Radiopharm. 21:603-614). The urethane linkage may be achieved using activated carbonate derivatives of the polyalkylene oxide, including but not limited to, carbonyl diimidazole-activated polyalkylene oxide as described in Beauchamp et al. (1983, Analyt. Biochem. 131:25-33) or Berger and Pizzo (1988, Blood 71:1641-1647). Preferably, the urethane linkage may be formed as described in U.S. pat. application Ser. No. 07/340,928 by Zalipsky et al., filed Apr. 19, 1989, which is incorporated by reference in its entirety herein. For example, and not by way of limitation, according to the method described by Zalipsky, methoxypoly(ethylene glycol)-N-succinimide carbonate (SC-PEG) or the similar but bifunctional derivative, poly(ethylene glycol)-bis-N-succinimide carbonate (BSC-PEG) may be used for conjugation to hemoglobin; alternatively, heterobifunctional derivatives of polyalkylene oxides may be used, in which one of the end-groups is N-succinimide carbonate and the other end group contains a different reactive functional group (as described in Zalipsky and Barany, 1986, Polymer Preprints, Am. Chem. Soc. Div. Poly. Chem. 27(1):1-2, which is incorporated by reference in its entirety herein).

N-hydroxysuccinimide derivatives of polyalkylene oxides may be prepared according to the method described in U.S. patent application Ser. No. 07/340,928, filed Apr. 19, 1989, by Zalipsky et al. For example, in a specific embodiment, SC-PEG may be prepared as follows:

Methoxypolyethylene glycol of molecular weight 5000 (Union Carbide, 60 g, 12 mmol) may be dissolved in toluene/dichloromethane (3:1, 200 ml) and treated with a toluene solution of phosgene (30 ml, 57 mmol) overnight. The solution may then be evaporated to dryness and the remainder of phosgene removed under vacuum. The residue may be redissolved in toluene/dichloromethane (2:1, 150 ml) and treated with solid N-hydroxysuccinimide (2.1 g, 18 mmol) followed by triethylamine (1.7 ml, 12 mmol). After 3 hours the solution may be filtered and evaporated to dryness. The residue may then be dissolved in warm (50° C.) ethyl acetate (600 ml), filtered from trace of insolubles and cooled to facilitate precipitation of the polymer. The product may be collected by filtration and then recrystallized once more from ethyl acetate. The product may be dried in vacuo over $P_2O_5$.

To determine the active carbonate content of the product, samples of the polymer may be reacted with a measured amount of benzylamine in dichloromethane and the excess of amine titrated with perchloric acid in dioxane.

Similarly, BSC-PEG may be prepared as follows:
Polyethylene glycol of molecular weight 4600 (Union Carbide, 50 g, 21.7 mequiv. OH) may be converted to the corresponding bis-N-succinimide carbonate using a toluene solution of phosgene (50 ml, 96.5 mmol) and then N-succinimide (3.8, 23 mmol) and triethylamine (3.2 ml, 23 mmol) following the procedure for producing SC-PEG described supra. After purification the product may be obtained as white powder.

In a particular embodiment of the invention, and not by way of limitation, monomeric Hb may be modified by monofunctional PEG. In a specific embodiment of the invention, bovine Hb may be modified with poly(ethylene glycol)-N-succinimide carbonate (SC-PEG) as follows:

bHb, reduced according to the method described in Section 5.1.1, supra, may be reacted with SC-PEG (having a molecular weight between 1900 and 10,000 Da) in buffer containing NaCl at a concentration between about 0.5 and 1.5 M and sodium phosphate at a concentration between about 0.1 and 1 M. Preferably, the molar ratio of SC-PEG to bHb is between about 10:1 and 50:1. The reaction may then be carried out at about 4° C., at a pH between about 7.5 and 8.5, under an inert atmosphere, for between one and six hours, and preferably between one and two hours. The relationship which has been observed between $P_{50}$ and the degree of modification is presented in Table II.

TABLE II

| | | Degree of Modification | | |
|---|---|---|---|---|
| | | 5% | 10% | 20% |
| $P_{50}$(mm Hg) of SC-PEG(5000)-bHb reacted in | 0.1M [Cl⁻] | 24 | 22 | 22 |
| | 0.5M [Cl⁻] | 28 | 24 | 24 |
| | 1.0M [Cl⁻] | 30 | 29 | 29 |

Alternatively, and not by way of limitation, polymeric hemoglobin may be produced by reacting hemoglobin first with bifunctional PEG and then with monofunctional PEG. In a specific embodiment of the invention, bovine Hb (bHb) may be first modified with poly-(ethylene glycol)-bis-N-hydroxysuccinimide carbonate (BSC-PEG) and then subsequently modified by SC-PEG as follows:

bHb reduced according to the method described in Section 5.1.1., supra, may be reacted with BSC-PEG (having a molecular weight between 1900 and 10,000 Da. in buffer containing NaCl at a concentration between about 0.5 and 1.5 M and sodium phosphate at a concentration between about 0.1 and 1 M. Preferably the molar ratio of BSC-PEG to bHb is between about 1:1 and 5:1. The reaction may then be carried out at about 4° C., at a pH between about 7.5 and 8.5, under an inert atmosphere, for between one and three hours. Bifunctional PEG-modified bHb has been observed to be associated with a higher $P_{50}$ than monofunctional PEG-modified bHb. Oxygen-binding affinity has been found to be associated with the degree of intramolecular and intermolecular cross-linking.

TABLE III

| Degree of modification of BSC-PEG(6000)-bHb* | $P_{50}$ (mm Hg) |
|---|---|
| 3% | 38.5 |
| 6% | 36.5 |
| 7.3% | 36.5 |

| Degree of modification of BSC-PEG(4600)-bHb* | $P_{50}$ (mm Hg) |
|---|---|
| 3% | 34 |
| 4.5% | 34 |
| 6% | 32.5 |

*All reactions are performed in 0.15M [Cl−]

Subsequently, SC-PEG (MW 1900–10,000 Da) may be added so that the molar ratio of SC-PEG to bHb is between about 5:1 and 20:1. Reaction may then be allowed to continue, under the same conditions, for between about two and four hours.

The amount of PEG modification may be controlled by altering the ratio of PEG to hemoglobin in the reaction mixture. According to a specific embodiment of the invention, between about 10 and 20 percent of bHb surface lysines are PEG-modified in order to result in substantial intravascular retention time. This corresponds to approximately between five and ten PEG molecules conjugated to one molecule of hemoglobin. Importantly, the degree of cross-linking may be altered in order to change the oxygen binding affinity or half-life of the modified hemoglobin (see Section 5.2, infra). If high molecular weight polyalkylene oxide is used, it may be desirable to decrease the degree of substitution.

5.1.3. Second Reduction

In order to provide for a high deoxyhemoglobin content and low methemoglobin levels, the deoxygenation and reduction step described in Section 5.1.1., supra, may be repeated. For example, after reaction with polyalkylene oxide has been completed, additional cysteine may be added to result in a final concentration between 1 and 100 mM, and preferably between 1 and 30 mM in an inert atmosphere. Modified hemoglobin may then be separated from other reactants using any method known in the art. In a preferred embodiment, the modified hemoglobin may be separated by ultrafiltration against a compatible buffer system at a pH of about 7.4.

A stabilizing agent, for example, but not limited to, glucose, may then be added to the modified hemoglobin solution. In a preferred embodiment of the invention, glucose is added to a concentration of about five percent.

5.1.4. Sterilization

Polyalkylene oxide-modified hemoglobin may then be sterilized by any method known in the art provided that said method does not result in oxidation and/or oxygenation of the modified hemoglobin or a conformational change. In a preferred, specific embodiment of the invention, the modified hemoglobin may be filter sterilized using a 0.2 micron membrane filter. The final product may be stored in a gas-impermeable blood bag at 4° C.

5.1.5. Characterization of Polylalkylene Oxide Modified Hemoglobin

The polyalkylene oxide modified hemoglobin may then be chemically characterized using methods known in the art. For example, the oxygen dissociation curve may be determined using standard techniques (for example, Imai et al., 1970, Biochim. Biophys. Acta 200: 189–196) allowing calculation of the $P_{50}$ value. Additional parameters which would be desirable to measure include the methemoglobin content, the viscosity, the osmolality, the pH, and the Hill constant; the effects of changes in pH on the oxygen saturation curve may be determined as described in Bartels (1971, Blood oxygen dissociation curves: Mammals. in "Respiration and Circulation", Altman and Dittmer, Eds., Federation of American Societies for Experimental Biology, Bethesda).

In vivo testing may be used to determine the safety and functional characteristics of polyalkylene oxide-modified bHb produced by the method of the invention. Such tests may include determination of acute toxicity reactions, blood circulating time of modified hemoglobin, assay for complement activation, determination of effectiveness of polyalkylene oxide-modified Hb in resuscitation efforts, and evaluation of immunogenicity of polyalkylene oxide-modified hemoglobin.

Acute toxicity studies may be performed in any suitable experimental animal. Preferably, a range of exposures may be tested; for example, by evaluating animals that have received a 50 or 70 percent exchange transfusion as compared to animals that have received a 100 percent exchange transfusion. Vital signs and visual observations should be recorded, and the animals may be sacrificed after a period of time estimated to correspond to one half-life of the hemoglobin formulation being tested. Histological evaluation using standard techniques may be used to determine the presence or absence of toxic effects on tissues including lung, kidney, liver, or brain.

Blood circulating time of polyalkylene oxide-modified Hb may, for example, and not by way of limitation, be evaluated by monitoring the concentration of hemoglobin in the plasma fraction (at 540 nm) of blood samples sequentially collected following exchange transfusion with modified Hb. Hemoglobin disappearance may be plotted as a function of time.

The efficacy of polyalkylene oxide-modified Hb in resuscitation efforts may be evaluated by replacing a substantial fraction of an experimental animal's blood volume (preferably more than 50 percent, more preferably more than 70 percent) with polyalkylene oxide-modified Hb at a concentration of 6-8% and then determining the effectiveness of polyalkylene oxide-modified Hb in promoting the survival and clinical stability (e.g. vital signs) of the test animal. Preferably, a comparison is made between the efficacy of the polyalkylene oxide-modified hemoglobin versus other blood substitutes (e.g. lactated Ringer's solution and/or whole blood).

The immunogenicity of polyalkylene oxide-modified Hb may be evaluated by inoculating an experimental animal with the polyalkylene oxide-modified Hb and subsequently testing for polyalkylene oxide-modified Hb specific antibodies using standard immunologic assays, including immunoprecipitation (further including immunoelectrophoresis techniques) and ELISA techniques.

5.2. Utility of the Invention

By providing for polyalkylene oxide-modified hemoglobin which is stable, effective at oxygen delivery and non-immunogenic, the present invention may be utilized as a safe and effective red blood cell substitute in humans as well as animals (e.g. veterinary uses).

The polyalkylene oxide-modified hemoglobin of the invention may be used in conjunction with any suitable pharmaceutical carrier, including physiologic saline compositions. The polyalkylene oxide-modified hemoglobin, in suitable carrier, may be stored in liquid formulation of 6-8% modified hemoglobin at 4° C.; alternatively, the polyalkylene oxide-modified hemoglobin may be desiccated. Furthermore, the polyalkylene oxide-modified hemoglobin may be stored at 4° C. and then rapidly warmed up for immediate transfusion using a microwave oven without causing any damage to the integrity of the product. Importantly, it has been observed that methemoglobin appears to form at an accelerated rate if oxyhemoglobin is present during storage of the polyalkylene oxide-modified hemoglobin; accordingly, it is preferable to include an oxygen scavenging agent and/or a reducing agent in pharmaceutical compositions so as to improve shelf life. Useful oxygen scavengers/reducing agents include but are not limited to cysteine, glucose, and mannitol.

The polyalkylene oxide-modified hemoglobin produced according to the invention may be used to treat a number of conditions and disorders, including, but not limited to, hypovolemia, shock, and anemia. The polyalkylene oxide-modified Hb of the invention may prove to be particularly useful in acute situations requiring immediate transfusion. For example, because polyalkylene oxide-modified Hb is stable for short periods at 37° C., a supply of pre-warmed blood substitute may be maintained in operating rooms and emergency medical facilities (including ambulances) to provide for immediate blood transfusions which are compatible with all blood types and which will not be associated with hypothermia in cases requiring massive transfusion.

Likewise, the polyalkylene oxide-modified Hb of the invention may be used to treat conditions in which red cell sludging occurs (e.g. sickle cell crisis) or in which endogenous red cells are inefficient or damaged. By altering cross-linking and/or substitution degree of the modified hemoglobin of the invention, the viscosity of the hemoglobin solution may be altered to facilitate clinical uses. By decreasing exposure to free iron, the polyalkylene oxide-modified Hb of the invention may be especially useful in the treatment of red blood cell disorders associated with iron deposition in tissues, including thalassemia.

Additionally, because the modified hemoglobin of the invention is smaller than red blood cells, it may be used to deliver oxygen to tissues which are inaccessible to red blood cells; for example, the polyalkylene oxide-modified hemoglobin of the invention may be used to traverse blood vessels obstructed by thrombus or constriction, and therefore may be therapeutically used in clinical settings including but not limited to myocardial infarction, cerebral infarction (stroke) and peripheral vascular diseases such as diabetes (including dry gangrene).

In further embodiments of the invention, the degree of conjugation of hemoglobin with polyalkylene oxide, or the extent of deoxygenation of hemoglobin prior to chemical modification, may be used to control the oxygen-binding affinity of the hemoglobin, thereby permitting the design of molecules appropriate to a variety of clinical situations. For example, a modified hemoglobin with a particularly high $P_{50}$ value would be desirable in clinical situations in which maximally efficient oxygen release to tissues would be advantageous, i.e., a patient with chronic obstructive pulmonary disease unable to oxygenate their own blood; a partial exchange transfusion of polyalkylene oxide-modified hemoglobin with a $P_{50}$ higher than physiologic hemoglobin, coupled with inspired air with high oxygen content, might be used to aid in oxygen delivery during critically acute clinical situations in conjunction with artificial respiratory support. Similarly, an exchange transfusion with polyalkylene oxide-modified hemoglobin, having a high $P_{50}$, might be useful in acute carbon monoxide poisoning. The present invention also envisions the design of a polyalkylene oxide-modified hemoglobin which binds carbon monoxide (CO) more tightly than native hemoglobin and therefore may be used to facilitate the elimination of CO and the liberation of native hemoglobin for oxygen transport. Likewise, the viscosity of the modified hemoglobin may be altered by using polyalkylene oxides of greater or lesser molecular weights (resulting in diminished or increased viscosity, respectively). For example, a low viscosity modified hemoglobin solution may be used to treat patients suffering from red blood cell sludging, for examples, patients in sickle cell crisis.

Importantly, in embodiments of the invention wherein the hemoglobin is derived from a non-human source, the polyalkylene oxide-modified Hb of the invention is substantially free of the potential risk of hepatitis, HIV, or HTLV infection and is also free of the risk of inducing graft versus host disease. Furthermore, the low immunogenicity of the polyalkylene oxide-modified Hb of the invention renders it particularly desirable for the treatment of patients who require repeated transfusions, for example patients with coagulopathies and bleeding disorders such as hemophilia.

6. EXAMPLE I: PRODUCTION OF A MONOMERIC BOVINE HEMOGLOBIN MODIFIED BY MONOFUNCTIONAL PEG

6.1. Materials and Methods

6.1.1. Bovine Hemoglobin

Bovine hemoglobin was obtained from Biopure, MA, and stored at −20° C.

6.1.2. Synthesis of Poly(ethylene Glycol)-N-Succinimide Carbonate

Methoxy PEG was obtained from Union Carbide and Nippon Oil and Fats Co. The PEG was activated according to the procedure set forth in U.S. patent Application No. 07/340,928, filed Apr. 19, 1989, by Zalipsky et al., as described in Section 5.1.2., supra.

6.1.3. Reduction of Hemoglobin

6% bovine hemoglobin was reacted with cysteine at a concentration of 30mM to deoxygenate oxy-bHb and to reduce Met-bHb. The process was carried out in a nitrogen atmosphere at 4° C. and pH 8 in the presence of 0.1M NaCl and 0.1M $NaHCO_3$. Reaction was then allowed to proceed for two hours.

Following completion of the first reduction step, ultrafiltration using a hollow fiber membrane from Amicon, MWCO=30,000 Da, was used to remove cysteine and any dimerized hemoglobin subunits.

6.1.4. Conjugation with Poly(Ethylene Glycol)-N-Succinimide Carbonate

Prior to PEG reaction, the hemoglobin-containing solution was adjusted to achieve a NaCl concentration of 0.75M, a $NaHCO_3$ concentration of 0.05M and a sodium phosphate concentration of 0.05M. SC-PEG (MW 5000) was then added at a molar ratio of 20:1. The reaction was allowed to proceed at 4° C., pH=8.0, under a nitrogen atmosphere, for two hours.

6.1.5. Second Reduction

After reaction with SC-PEG was completed, additional cysteine was added to a concentration of 30 mM to convert any remaining oxy-bHb and Met-bHb. After two hours, ultrafiltration was repeated against a solution containing 0.1 M NaCl, 30 mM $NaHCO_3$, 5mM KCl, 3 mM $CaCl_2$ and 0.9 mM $MgCl_2$, pH=7.4 sodium ascorbate 10 mM) and glucose Were then added to the PEG-bHb solution to a final concentration of 5% (w/v). The product was then filter sterilized using a 0.2 micron Zetapor membrane filter.

6.2 Results and Discussion

The $P_{50}$ of the above PEG-bHb was 29mm Hg (Table IV). Substitution degree was 15%, colloid osmolality was 24 mm Hg, and the product was shown to be free of endotoxins (using the LAL test), pyrogens (using the U.S.P. pyrogen test) and free iron using the ferrozine assay method (Carter, 1971, Analyt. Biochem. 40:450–458). Half-life of this example injected into rats after a 70 percent exchange transfusion was approximately nine hours (Table IV). Formation of Met-bHb in rat intravasculature was substantially lower than that of unmodified hemoglobin (Table IV)

7. EXAMPLE II: DEOXYGENATION OF HEMOGLOBIN USING A GAS PERMEABLE MEMBRANE

The preparation of bovine hemoglobin and SC-PEG was performed as described in Section 6, Example I, supra.

For reduction of hemoglobin, 6% bovine hemoglobin was recirculated through gas-permeable hollow fiber membranes (commercially known as oxygenators) against pressurized nitrogen to achieve gas exchange resulting in deoxygenation of hemoglobin. The process was carried out in a nitrogen atmosphere at 4° C. and pH 8 in the presence of 0.1 M NaCl and 0.1 M $Na_2HPO_4$. Reaction was then allowed to proceed until more than 80% deoxyHb was obtained.

Deoxygenated bHb was then conjugated to PEG and subjected to second reduction as described in Section 6, Example I except that sodium ascorbate was not added and glucose was added to a concentration of three percent.

The physical and chemical properties of SC-PEG-bHb prepared in this manner are shown in Table IV. The observed $p_{50}$ was 24 mmHg, the substitution degree was 16 percent, and the half life of the modified hemoglobin in vivo, measured in rats given a 70 percent exchange transfusion of the modified hemoglobin, was 9.6 hours (see Table V).

8. EXAMPLE III: CONJUGATION OF HEMOGLOBIN TO MONOFUNCTIONAL PEG AT A 30:1 MOLAR RATIO

Bovine hemoglobin was prepared, deoxygenated and reduced as described in Section 7, Example II. Conjugation with SC-PEG was also the same with the exception that SC-PEG (MW 3000) was added at a molar ratio of 30:1. The second reduction was then performed as described in Section 7, Example II.

The physical and chemical properties of SC-PEG-bHb prepared in this manner is shown in Table IV. The observed $p_{50}$ was 25 mmHg, the substitution degree was 32 percent, and the half-life observed in a 70 percent exchange transfusion in rats was 12.4 hours (see Table V).

9. EXAMPLE IV: CONJUGATION OF HEMOGLOBIN TO MONOFUNCTIONAL PEG AT A 40:1 MOLAR RATIO

Bovine hemoglobin was modified as described in Section 8, Example III, supra, except that SC-PEG (MW 2000) was added at a molar ratio of 40:1.

As shown in Table IV, hemoglobin prepared in this manner was observed to exhibit $p_{50}$ of 20 mmHg and a substitution degree of 50 percent. As shown in Table V, its half-life in a 70 percent exchange transfusion of rats was found to be 13.0 hours.

10. EXAMPLE V: PRODUCTION OF POLYMERIZED BOVINE HEMOGLOBIN MODIFIED FIRST BY BIFUNCTIONAL PEG AND THEN FURTHER MODIFIED BY MONOFUNCTIONAL PEG

10.1. Materials and Methods

10.1.1. Bovine Hemoglobin

Bovine hemoglobin was obtained from Biopure, MA, and stored frozen at −20° C.

10.1.2. Synthesis of Poly(Ethylene Glycol)-Bis-N-Succinimide Carbonate

BSC-PEG was prepared according to methods set forth in U.S. patent application No. 07/340,928, filed Apr. 989, by Zalipsky et al., as described in Section 5.1.2., supra.

10.1.3. Reduction of Hemoglobin

Six percent bovine hemoglobin was reacted with 30 mM cysteine under a nitrogen atmosphere at 4° C. and pH=8.0 in the presence of 0.1M NaCl and 0.1M $NaHCO_3$. Reaction was allowed to proceed for two hours, after which the solution was subjected to ultrafiltration, as described in 6.1.3., supra.

10.1.4. Conjugation With BSC-PGE

Prior to conjugation with PEG, the hemoglobin-and with SC-PEG containing solution was adjusted to achieve NaCl concentration of 0.75M, a NaHCO$_3$ concentration of 0.05M and a sodium phosphate concentration of 0.05M. BSC-PEG (MW 4600) was added at a molar ratio (BSC-PEG:bHb) of 2:1. Reaction was carried out at 4° C., pH=8.0, under a nitrogen atmosphere for an hour. Subsequently, SC-PEG (MW 5000) was added at a molar ratio (SC-PEG:bHb) of 10:1. Reaction was allowed to proceed for another hour under the same conditions.

10.1.5. Second Reduction

After reaction with BSC-PEG and SC-PEG was completed, additional cysteine was added to a concentration of 10 mM in order to remove any remaining oxy-bHb and Met-bHb. After two hours, ultrafiltration was repeated against a solution containing 0.1 M NaCl, 0.1 M NaHCO$_3$.5 mM KCl, 3 mM CaCl$_2$, and 0.9 mM MgCl$_2$, pH=7.4 sodium ascorbate (10 mM) and glucose were then added to the PEG-bHb solution to a final concentration of 5% (w/v). The product was filter sterilized using a 0.2 micron Zetapore membrane filter.

10.2. Results of Discussion

The P$_{50}$ of the above PEG-bHb was 32mm Hg. Substitution degree was 10 percent, colloid osmolality was 22mm Hg, and the product shown to be free of endotoxins, pyrogens, and free iron using methods described supra. Half-life of this example injected into rats after a 70 percent exchange transfusion was 19 hours. This example was associated with intravascular Met-bHb formation of 12% in ats.

TABLE IV

| | CHEMISTRY OF PEG-Hb | | | | | |
|---|---|---|---|---|---|---|
| EXAMPLE | CONTROL | I | II | III | IV | V |
| PEG | none | SC- | SC- | SC- | SC- | BSC- & SC- |
| M.W. (PEG) | | 5000 | 5000 | 3000 | 2000 | 5000 5000 |
| % Modification | 0 | 15 | 15 | 31 | 50 | 6 |
| Avg. Na. of PEGs on Hb | 0 | 7.2 | 7.7 | 14.9 | 24 | 3.8 |
| Total M.W. of PEG-Hb (KD) | 64.5 | 100.5 | 103.5 | 109.2 | 112.5 | 76.5 |
| Concentration (%) | 5.5 | 5.0 | 5.7 | 5.5 | 5.4 | 5.0 |
| p$_{50}$ (mmHg) | 25 | 22 | 25 | 25 | 20 | 27 |
| MetHb (%) | <5 | 6 | <5 | <5 | <5 | 2 |
| Viscosity (cp) | 3.0 | 3.6 | 4.5 | 3.8 | 3.2 | 4.0 |
| Osmotic Press. (mmHg) | 22 | 24 | 22 | 22 | 22 | 20 |
| Hill Coeff. | 2.4 | 2.58 | 2.2 | 2.05 | 1.8 | 2.2 |
| Free Iron (microg/dL) | 24 | ND | 27 | 20 | 20 | ND |
| Additives | | | | | | |
| Ascorbate (mM) | 0 | 10 | 0 | 0 | 0 | 10 |
| Dextrose (%) | 3 | 5 | 3 | 3 | 3 | 5 |
| Endotoxin (EU) | <.1 | <.1 | <.1 | <.1 | <.1 | <.1 |

11. EXAMPLE VI: IN VIVO STUDIES

The results of in vivo studies, in which rats were given a 70 percent exchange transfusion of hemoglobin prepared according to Examples I-V or control (native bovine hemoglobin) are shown in Table V (bracketed numbers are values obtained in rats that were not transfused). Note that the breathing rate decreased slightly, and the blood pressure increased by at most about 30–35 percent relative to control, showing a good physiologic response to the exchange transfusion.

TABLE V

| | IN VIVO DATA IN RATS (AT 70% EXCHANGE TRANSFUSION) | | | | | |
|---|---|---|---|---|---|---|
| EXAMPLE | CONTROL | I | II | III | IV | V |
| Half-life (hr) | 1.5 | 8.9 | 9.6 | 12.4 | 13.0 | 18.8 |
| Met-Hb (%) at Half-life | 16.5 | 29.3 | 5.8 | 13.8 | 18.0 | 12.0 |
| Mean Arterial Press. (mmHg) | 90 [131] | 102 [138] | 119 [141] | 132 [150] | 129 [137] | 97 [119] |
| Heart Rate [min$^{-1}$] | 304 [376] | 392 [404] | 408 [429] | 408 [368] | 432 [422] | 423 [360] |
| Breathing [min$^{-1}$] | 100 [79] | 117 [110] | 104 [78] | 79 [87] | 83 [73] | 90 [90] |

12 EXAMPLE VII: REDUCING AGENTS IN BOVINE HEMOGLOBIN SOLUTION

12.1. Materials and Methods 30 mM of each reducing agent tested, including cysteine, glutathione, N-acetyl cysteine, N-acetyl methionine and sodium ascorbate, was added to 5% bovine hemoglobin solution containing 0.1M Na phosphate, 0.1M NaHCO$_3$ and 0.1M NaCl, with pH=7.4 and at 4° C., under an inert atmosphere. 20 hours later, the deoxyhemoglobin (deoxy Hb), Met Hb and free iron concentrations were determined. Met Hb and deoxy Hb concentrations were measured using an OSM3 Hemoximeter (Radiometer) and free iron was determined by the ferrozine assay method (Carter, 1971, Analyt. Biochem. 40:450–458).

12.2. Results

Of all reducing agents tested, cysteine was associated with the highest levels of deoxyhemoglobin and the lowest levels of methemoglobin and free iron of any of the reducing agents tested (Table V). The efficacy of cystein is presumably due to its ability to function as both an oxygen scavenger and reducing agent.

TABLE VI

| | Cysteine | Na-Ascorbate | GSH | N-acetyl cysteine | N-acetyl methionine |
|---|---|---|---|---|---|
| dexoy Hb (%) | 97.6 | 96.7 | 9.7 | 0 | 0 |
| Met Hb (%) | 0.8 | 4.1 | 11.9 | 18.8 | 19.6 |
| Free iron (microg/dl) | 4.26 | 233.7 | | | |

13. EXAMPLE VIII: PARTIAL DEOXYGENATION OF HEMOGLOBIN BY GAS EXCHANGE, AND ITS MODIFICATION USING MONOFUNCTIONALLY ACTIVATED POLYETHYLENE GLYCOL

Bovine hemoglobin was purchased from Biopure, Boston, MA, and prepared at a concentration of 6% (g/dl) containing 0.5 M NaCl, 0.1 M Na$_2$HPO$_4$ and 0.05 M NaHCO$_3$. The final pH was adjusted to 7.8, and the temperature of the entire process was maintained at 4°–6°. Deoxygenation of this solution, which originally contained about 94–96 percent oxyHb was carried out by preparing a sealed vessel containing the Hb solution with its gas phase filled with nitrogen and recirculating the Hb solution through a G-240/11/Celgard TM gas-exchange device while the space outside the fibers was continuously replenished with pressurized nitrogen at 10 p.s.i. The process of deoxygenation was continued until the percent deoxyHb was determined to be 20, 5, 50, 70, 90, or 95 percent using a commercial OSM3 Hemoximeter (Radiometer, Copenhagen).

Following preconditioning by deoxygenation, polyethylene glycol-succinimidyl carbonate (SC-PEG, M.W. 5141) was carefully added into the Hb solution.

SC-PEG is a monofunctional PEG polymer having one activated end, namely, succinimidyl carbonate. N-hydroxy succinimide becomes the leaving group upon reaction with lysines of hemoglobin. The molar ratio between SC-PEG:Hb was 12:1. The powdery PEG was rapidly vortexed into the Hb solution to allow homogeneous mixing, and the PEG-reaction was allowed to proceed for 1½-2 hours. During this time the reaction vessel was carefully guarded against exposure to air in order to maintain the level of deoxyHb. After PEG-modification was complete, the level of deoxyHb was again measured (see Table VII).

Purification was carried out using a hollow-fiber ultrafiltration device with M.W. cutoff of 50 kD that is commercially available from American Fluid, Richboro, Pa. The advantage of this device relative to conventional tangential flat ultrafiltration membranes is its easy handling of viscous protein solutions such as the 6% PEG-Hb solution. Following purification, the $P_{50}$ of the PEG-Hb was determined by a Hemox-Analyzer (TCS Medical Products Co., Huntington Valley, Pa.). As shown in Table VII, the highest $P_{50}$ values were obtained when the percentage of deoxyHb prior to modification was 50 or 70 percent. Based on HPLC chromatograms, the PEG-hemoglobin thus produced appeared to be very homogeneous in that it was found to consist of only tetrameric entities and to be substantially free of polymerized hemoglobin. The average number of PEG residues bound to one Hb molecule was found to be about 7.7. The observed viscosity of this product at 6 percent (g/dl) and 37° C. was 4.2 cp, and its colloid osmotic pressure was found to be 24 mmHg.

TABLE VII

| % deoxyHb (before PEGylation) | % deoxyHb (after PEGylation) | $P_{50}$ (mmHg) | Hill coeff. |
|---|---|---|---|
| 0 | 0 | 18 | 1.7 |
| 20 | 18 | 18 | 1.7 |
| 35 | 33 | 18 | 1.7 |
| 50 | 48 | 24 | 2.0 |
| 70 | 68 | 28 | 2.2 |
| 90 | 88 | 22 | 2.0 |
| 95 | 92 | 22 | 2.0 |

*The native stroma-free bHb from Biopure, Boston, MA has $P_{50}$ of 28 mmHg and Hill Coefficient 2.3

14. EXAMPLE IX: PARTIAL DEOXYGENATION OF HEMOGLOBIN BY A CHEMICAL REDUCING AGENT, AND ITS MODIFICATION USING MONOFUNCTIONALLY ACTIVATED POLYETHYLENE GLYCOL

6% Bovine hemoglobin (see Section 5, supra) was deoxygenated using the chemical reducing agent sodium bisulfite and then modified using monofunctionally activated SC-PEG as described in Section 13, supra. Table VIII shows the p50 and Hill Coefficient of PEG-hemoglobin produced using hemoglobin preconditioned by exposure to various concentrations of sodium bisulfite prior to PEGylation. After the sodium bisulfite was added, one hour was allowed to elapse prior to PEGylation, to allow for deoxygenation to stabilize As shown in Table VIII, optimal p50 and Hill Coefficient values were observed when hemoglobin was exposed to 100 mM sodium bisulfite, so as to produce a preconditioned hemoglobin which was 75 percent deoxyHb.

TABLE VIII

| Sodium Bisulfite Concentration (mM) | % deoxyHb (before PEGylation) | $P_{50}$ of PEG-Hb (mmHg) | Hill Coefficient |
|---|---|---|---|
| 30 | 59 | 18.5 | 1.8 |
| 50 | 63 | 19.0 | 1.8 |
| 100 | 75 | 28.0 | 2.2 |
| 175 | 95-100 | 24.0 | 2.0 |

15. EXAMPLE X: PARTIAL DEOXYGENATION OF HEMOGLOBIN BY GAS EXCHANGE, AND ITS MODIFICATION USING BIFUNCTIONALLY ACTIVATED POLYETHYLENE GLYCOL

A 3 percent solution of bovine hemoglobin was deoxygenated, and modified essentially as described in Section 13, supra, except that a bifunctional activated polyethylene glycol, namely, polyethylene glycol-bis-succinimidyl carbonate (BSC-PEG, M.W. 5000), at a mole ratio of BSC-PEG:Hb of 2.5:1, was used to yield crosslinked hemoglobin. Based on HPLC analysis, approximately 50 percent of the Hb product appeared to be polymerized (two molecules of Hb bound together by one molecule of PEG), and the other 50 percent appeared to be tetrameric hemoglobin intramolecularly crosslinked by PEG. The viscosity of a 6 percent (g/dl) solution of this product was found to be 4.5 cp at 37° C., and its colloid osmotic pressure was found to be 20 mmHg. The percentage of deoxyHb prior to and following modification and the $P_{50}$ of modified hemoglobin were also measured as described in Section 5, supra (see Table IX. The highest $P_{50}$ values were observed to be associated with 61 and 76 percent deoxyHb prior to modification.

TABLE IX

| % deoxyHb (before PEGylation) | % deoxyHb (after PEGylation) | $P_{50}$ (mmHg) | Hill coeff. |
|---|---|---|---|
| 0 | 0 | 20 | 1.8 |
| 25 | 23 | 22 | 1.9 |
| 45 | 43 | 25 | 2.0 |
| 61 | 60 | 30 | 2.3 |
| 76 | 74 | 31 | 2.3 |
| 93 | 91 | 26 | 2.0 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the amended claims.

Various publications are cited herein, the disclosures of which are incorporated by reference in their entirety.

What is claimed is:

1. A chemically modified hemoglobin comprising hemoglobin conjugated to polyalkylene oxide by a urethane linkage and having a $P_{50}$ greater than 20 mmHg.

2. The chemically modified hemoglobin of claim 1 in which the polyalkylene oxide is poly(ethylene glycol).

3. The chemically modified hemoglobin of claim 1 in which the hemoglobin is intramolecularly crosslinked.

4. The chemically modified hemoglobin of claim 1 in which the hemoglobin is intermolecularly crosslinked.

5. A pharmaceutical composition comprising the chemically modified hemoglobin of claim 1 in a suitable pharmacutical carrier.

6. The chemically modified hemoglobin of claim 1, in which the hemoglobin is human hemoglobin.

7. The chemically modified hemoglobin of claim 1, in which the hemoglobin is non-human hemoglobin.

8. The chemically modified hemoglobin of claim 7, in which the non-human hemoglobin is bovine hemoglobin.

* * * * *

UNITED STATES PATENT AND TRADEMARK OFFICE
CERTIFICATE OF CORRECTION

PATENT NO. : 5,234,903

DATED : August 10, 1993

INVENTOR(S) : Nho et al.

It is certified that error appears in the above-identified patent and that said Letters Patent is hereby corrected as shown below:

Column 1, lines 40-41, "-N-succinimdie" should read -- -N-succinimide--.

Column 1, line 52, "EPG" should read --PEG--.

Column 1, line 53, "Polymerizated" should read --Polymerized--.

Column 1, line 57, "Materails" should read --Materials--.

Column 2, line 6, "chemical Reduction" should read --Chemical Reducing--.

Column 3, line 38, "N. Engl J. Med." should read --N. Engl. J. Med.--.

Column 4, line 26, "consisting two" should read --consisting of two--.

Column 6, line 53, "mddified" should read --modified--.

UNITED STATES PATENT AND TRADEMARK OFFICE
CERTIFICATE OF CORRECTION

PATENT NO. : 5,234,903
DATED : August 10, 1993
INVENTOR(S) : Nho et al.

It is certified that error appears in the above-identified patent and that said Letters Patent is hereby corrected as shown below:

Column 9, line 54, "Section 5 1.1.1.," should read --Section 5.1.1.1.,--.

Column 19, line 39, "glucose Were" should read --glucose were--.

Column 20, line 61, "Apr. 989" should read --April 19, 1989--.

Column 21, line 3, "BSC-PGE" should read --BSC-PEG--.

Column 21, lines 5-6, "hemoglobin-and with" should read --hemoglobin-and then with--.

Column 21, line 7, "achieve NaCl" should read --achieve a NaCl--.

Column 22, line 46, in Table VI, first column, "dexoy Hb" should read "deoxy Hb--.

UNITED STATES PATENT AND TRADEMARK OFFICE
CERTIFICATE OF CORRECTION

PATENT NO. : 5,234,903

DATED : August 10, 1993

INVENTOR(S) : Nho et al.

It is certified that error appears in the above-identified patent and that said Letters Patent is hereby corrected as shown below:

Column 23, line 4, "20, 5," should read --20, 35,--.

Column 24, lines 23-24, "hemoglobin was deoxygenated," should read --hemoglobin was prepared, deoxygenated,--.

Column 25, line 7, "pharmacutical carrier" should read --pharmaceutical carrier-.

Signed and Sealed this

Twenty-fourth Day of January, 1995

*Attest:*

BRUCE LEHMAN

*Attesting Officer*     *Commissioner of Patents and Trademarks*